United States Patent
Wei

(10) Patent No.: US 8,062,447 B2
(45) Date of Patent: Nov. 22, 2011

(54) METHOD OF MANUFACTURING A VISCOELASTIC BANDAGE

(75) Inventor: Xu Wei, Jiangsu Province (CN)

(73) Assignee: Caremax Co., Ltd., Jiangsu Province (CN)

( * ) Notice: Subject to any disclaimer, the term of this patent is extended or adjusted under 35 U.S.C. 154(b) by 879 days.

(21) Appl. No.: 12/005,328

(22) Filed: Dec. 26, 2007

(65) Prior Publication Data

US 2008/0121338 A1     May 29, 2008

Related U.S. Application Data

(63) Continuation of application No. PCT/CN2006/002432, filed on Sep. 18, 2006.

(30) Foreign Application Priority Data

Jun. 12, 2006 (CN) .......................... 2006 1 0085983

(51) Int. Cl.
*B32B 37/00* (2006.01)

(52) U.S. Cl. .................. 156/148; 156/160; 156/229

(58) Field of Classification Search .................. 156/160, 156/161, 148, 163, 164, 229
See application file for complete search history.

(56) References Cited

U.S. PATENT DOCUMENTS

| | | | |
|---|---|---|---|
| 5,894,032 A | 4/1999 | Green et al. | |
| 2005/0084647 A1* | 4/2005 | Menzies et al. | 428/99 |
| 2008/0014387 A1* | 1/2008 | Murphy et al. | 428/34.1 |

FOREIGN PATENT DOCUMENTS

| | | |
|---|---|---|
| CN | 1568916 | 1/2005 |
| CN | 1589911 | 3/2005 |
| CN | 1600376 | 3/2005 |
| JP | 08-038545 | 2/1996 |
| JP | 2002336295 | 11/2002 |
| WO | WO 2007/143890 A1 | 12/2007 |

* cited by examiner

*Primary Examiner* — Jeff Aftergut
(74) *Attorney, Agent, or Firm* — Simpson & Simpson, PLLC

(57) ABSTRACT

A manufacturing method of a viscoelastic bandage, having a nonwoven fabric, an elastane yarn, base cloth, and natural latex or synthetic latex as main raw materials. A viscoelastic bandage suitable for such trades as medical bandaging, industrial operation protection, field operation and sports protection can be manufactured after going through the following steps, manufacturing of the elastic base cloth→surface treatment→anti-seizing treatment→adhesive coating process. Provides high production efficiency and low cost, suitable for an industrialized mass production, with outstanding comprehensive processing economy and very powerful market competitiveness. Besides, the product has the following properties and characteristics: (1) Breaking tenacity up to 180-220 KN/m; (2) tensile ratio up to 80-120%; (3) good air permeability; (4) perfect stripping uniformity; (5) stable product property and longer storage life; and (6) attractive appearance; there is no rough fiber on the exterior surface of the nonwoven fabric any more.

3 Claims, 3 Drawing Sheets

METHOD OF MANUFACTURING A VISCOELASTIC BANDAGE

CROSS-REFERENCE TO RELATED APPLICATIONS

This application is filed under 35 U.S.C. §120 and §365(c) as a continuation of International Patent Application PCT/CN2006/002432, filed Sep. 18, 2006, which application is incorporated herein by reference. This application also claims priority from Chinese Patent Application No. 200610085983.9, filed Jun. 12, 2006, which application is incorporated herein by reference.

FIELD OF THE INVENTION

The present invention relates to a viscoelastic bandage used in such trades as medical bandaging, industrial operation protection, field operation and sports protection, and particularly to a manufacturing method for viscoelastic bandages.

BACKGROUND OF THE INVENTION

As a medical or protective article, elastic bandages have been widely used in medical bandaging, industrial operation protection, field operation, sports protection, etc. In sports, for example, muscles can become relaxed during prolonged exercise due to hemangiectasis and oxygen supply shortage. Elasticity can be appropriately regulated with an elastic bandage. Muscle relaxation can be deferred through active advance physical vein compression, making muscle exercise persist longer. Meanwhile, stronger reactive bracing can be provided through bandaging, making muscle produce more intensive explosive power.

Prior elastic bandages can be classified into two kinds, viscoelastic bandages and self-viscoelastic bandages. The self-viscoelastic bandage refers to a bandage that has mutual viscosity between adhesive layers themselves of the bandage, which generally has no bonding characteristic with other objects or human body; while the viscoelastic bandage refers to a bandage whose adhesive layer has both self-viscosity and else-viscosity. Therefore, in usage, the self-viscoelastic bandage may glide on an object or human body applied with the bandage, while the viscoelastic bandage will not. On the other hand, in aspects of usage environment and scope, the self-viscoelastic bandage is narrow in usage scope, while the viscoelastic bandage use is wider in scope. For example, fracture bandaging requires stronger bandaging protection, so as to prevent further movement. Here it would be better to adopt the viscoelastic bandage. Again for example, the self-viscoelastic bandage is poor at heat resistance and low temperature resistance, and not suitable to be used near the equator, while the viscoelastic bandage is better in this aspect.

It can be known from the above introduction that for a viscoelastic bandage with a wide usage scope, it is more important to possess comprehensive processing economy and production efficiency of industrialized mass production in addition to satisfying usage property and quality requirements (i.e., suitable elasticity, strength, air permeability and viscosity). However, as far as the applicant knows, a manufacturing process of elastic base cloth of the traditional typical viscoelastic bandage is implemented via weaving. To be specific, the process includes aligning inelastic fibers and elastic fibers according to a certain spacing proportion along a warp thread direction, and by weaving a weft thread using a shuttle loom or a shuttleless loom, etc. Therefore, it is impossible to improve the processing efficiency due to restrictions from the two physical actions of longitudinal warp thread pulling and transverse weft thread weaving. The production efficiency will be still lower if an old-style shuttle loom is adopted (about 4 meters/minute); besides, it is easy for a shuttle with reciprocating motion to interrupt the warp thread, resulting in a great number of rejects and defectives and poor economic efficiency. As for prior advanced, looms, such as rapier looms and ball looms, although the production efficiency has somewhat been improved, the comprehensive processing economy is not ideal either due to high manufacturing cost of the equipment.

SUMMARY OF THE INVENTION

The present invention provides a method of manufacturing a viscoelastic bandage, with a purpose to resolve the problems of low processing efficiency and poor comprehensive processing economy with the prior viscoelastic bandage.

The present invention adopts the following technical solution in order to attain the above purpose. A method of manufacturing a viscoelastic bandage is provided that includes the sequential steps as below:

(1) Manufacture of Elastic Base Cloth

A. Raw Materials

Nonwoven fabric; elastane yarn; and base cloth.

Use natural latex or synthetic latex, diluted with water according to latex:water=1:1-2, as an adhesive for spare use.

B. Process

Feed a nonwoven fabric, an elastane yarn and base cloth through different send rolls. Meanwhile, coat the interior surface of the nonwoven fabric or the base cloth with the adhesive. Then laminate the nonwoven fabric and the base cloth with a press roll after superposing the nonwoven fabric and the base cloth according to the position relation of sandwiching the elastane yarn. Heat to evaporate water in the adhesive, so as to obtain composite elastic base cloth. In the process, pressure of the press roll is 2-4 kilograms, preferably 2.5-3.5 kilograms; and the heating temperature is controlled at 80-180° C., most preferably 80-120° C.

(2) Surface Treatment of Elastic Base Cloth

A. Raw Materials

Elastic Base Cloth.

Use natural latex or deproteinized latex or synthetic latex, diluted with water according to latex:water=1:2-6, as a surface treatment agent for spare use.

Use glacial acetic acid or hydrochloric acid, diluted with water according to acid:water=1:8-12, as an acid curing agent for spare use.

B. Process

Choose one of the following two processes:

a. Double-Sided Coating

Dip coat the elastic base cloth, after being guided by a guide roll, with the surface treatment agent in a tank. Then coat at least exterior surface of the nonwoven fabric with the acid curing agent to cure. Then wash with water in a rinse tank. Finally dry by extruding with the press roll and then sending to an oven, with the oven temperature at 80-180° C.

b. Single-Sided Coating

With the elastic base cloth being guided by the guide roll, coat exterior surface of the nonwoven fabric with the surface treatment agent. Then heat to evaporate water in the surface treatment agent, with the heating temperature controlled at 80-180° C.

(3) Coating of Elastic Base Cloth with Adhesive

A. Raw Materials

The elastic base cloth having processed in the last step.

Use a hot melt adhesive, a water-based adhesive or a solvent adhesive as the adhesive B. Process Coat one side of the elastic base cloth, having processed in the last step, with the adhesive through guidance of the guide roll, and then obtain the final product through after-treatment and winding.

The relevant contents in the above technical solution are explained as below:

1. In order to prevent difficulty in de-winding the elastic base cloth coated with the adhesive in the above Step (3), make the product stripping as easy and uniform as possible, and meanwhile make the adhesive permeate to the other side of the elastic base cloth, an anti-seizing treatment can be inserted between surface treatment of the elastic base cloth and coating of the elastic base cloth with the adhesive, that is, coat one side of the elastic base cloth with silicone oil after the surface treatment of the elastic base cloth. The specific steps are as below:

A. Raw Materials

The elastic base cloth having received surface treatment.

Formulation of the anti-seizing treatment agent is as below:

| Composition | Content |
| --- | --- |
| Silicone rubber | 100 parts by weight ± 10% |
| Methyltriethoxysilane | 35 parts by weight ± 10% |
| Dibutyltin dilaurate | 8 parts by weight ± 10% |
| 120# solvent gasoline | 800 parts by weight ± 10% |

B. Process

With the elastic base cloth, having received surface treatment, being guided by the guide roll, coat exterior surface of the nonwoven fabric with the anti-seizing treatment agent. Then heat to evaporate solvent in the anti-seizing treatment agent, with the heating temperature controlled at 130-200° C., preferably 160-180° C.

2. In the manufacture of the elastic base cloth in the above Step (1) of the solution, in order to improve production efficiency, laminate the nonwoven fabric, the elastane yarn and the base cloth with the press roll and heat in a continuous laminating and drying way through the combination of a drying cylinder and the press roll. That is, the nonwoven fabric, the elastane yarn and the base cloth are superposed and wound to go through the drying cylinder, and meanwhile some press rolls are positioned at exterior surface of the drying cylinder in circumferential direction, such that the elastic base cloth is laminated on one side (the pressure is regulated via clearance between the drying cylinder and the press roll) and heated on the other side (the heating temperature is set via a heating source in the drying cylinder) when between the drying cylinder and the press roll. Refer to FIG. 1.

3. In the surface treatment of the elastic base cloth in the above Step (2) of the solution, a temperature gradient with at least two segments is adopted in the oven from the inlet to the outlet, with the temperature range controlled at 100-160° C.

4. The individual process step in the above solution can either be linked together into a consecutive production line, or form independently individual production line.

Because of application of the above technical solution, the present invention has the following advantages and effects compared to the prior art:

1. It can be seen from FIG. 1 that, if the dimension limitation of the raw materials is not considered, the production efficiency of the manufacturing method of the elastic base cloth of the present invention is subject to water evaporation speed, while the raw materials of the nonwoven fabric, the elastane yarn and the base cloth are all subject to a pulling force, without an influence from transverse weft thread weaving in the weaving method. Therefore, a higher production speed can be kept through increasing number of the drying cylinders without a possibility of damaging the elastic bandage, improving production efficiency and economic performance.

2. Making use of the mechanism that natural latex, deproteinized latex or synthetic latex has a good film-forming characteristic, the present invention forms a protective film on the exterior surface of the nonwoven fabric through the surface treatment step of the elastic base cloth, thus achieving the following results:

(1) Form a protective film on the exterior surface of the nonwoven fabric through surface treatment, thus securing fiber fastness and changing the appearance.

(2) Improve compound fastness of the elastic base cloth through the surface treatment, the elastic base cloth finally coated with the adhesive not being torn any more to affect the usage property.

(3) Improve tensile strength of the entire elastic base cloth after the surface treatment.

3. Coating one side of the elastic base cloth with silicone oil in the anti-seizing treatment step, the present invention effectively prevents difficulty in de-winding the elastic base cloth coated with the adhesive, making the product stripping as easy and uniform as possible and meanwhile the adhesive permeate to the other side of the elastic base cloth.

4. The present invention has a high production efficiency and a low cost, suitable for an industrialized mass production, with outstanding comprehensive processing economy and very powerful market competitiveness.

5. The products of the present invention have the following properties and characteristics:

(1) Suitable strength of the base cloth, with the breaking tenacity up to 180-220 KN/m;

(2) suitable elasticity, with the tensile ratio up to 80-120%;

(3) good air permeability;

(4) perfect usability; after slitting and rewinding, each small roll has very good stripping uniformity from end to end;

(5) longer storage life, ensuring good adhesion of the adhesive in the usual environment without permeation or transfer; and (6) attractive appearance; there is no rough fiber on the exterior surface of the nonwoven fabric any more.

DETAILED DESCRIPTION OF THE INVENTION

The present invention will be further described below with reference to drawings and embodiments.

Embodiment: A method of manufacturing a viscoelastic bandage is provided including the following four steps:

Manufacture of elastic base cloth→surface treatment of elastic base cloth→anti-seizing treatment of elastic base cloth→coating of elastic base cloth with adhesive Step one: Manufacture of Elastic Base Cloth A. Raw Materials a. Nonwoven fabric. A nonwoven fabric being soft, light and thin should be set as the benchmark in view of product function, with economic performance taken into consideration. The nonwoven fabric is a carrier of the adhesive, and should have certain waterproof and anti-leaking properties. Therefore, such processes as hot rolling process and spun-bonded process can be adopted to produce a nonwoven fabric with mature process and good economic performance.

b. Elastane yarn. Spandex bare yarns or covered yarns can be adopted.

c. Base cloth. All-cotton fabrics are more considered for medical supplies. Base cloth without elasticity or with little elasticity can be adopted.

d. Adhesive. Use natural latex or synthetic latex, diluted with water according to latex:water=1:1.5, as an adhesive for spare use. This is because natural latex or synthetic latex is the most general adhesive raw material.

B. Process

Figure 1:
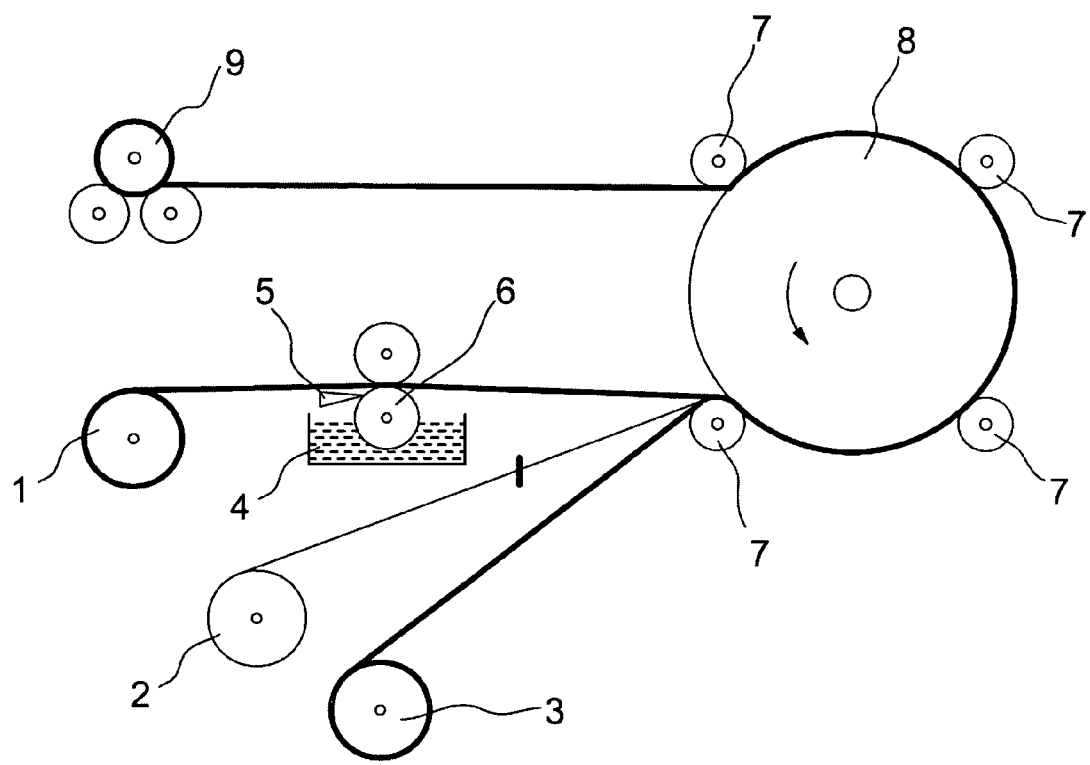
FIG. 1 is a schematic drawing of the manufacturing process flow of the elastic base cloth.

As shown in FIG. 1, send the nonwoven fabric, the elastane yarn and the base cloth simultaneously from the nonwoven fabric send roll 1, the elastane yarn send roll 2 and the base cloth send roll 3, respectively. Coat the interior surface of the nonwoven fabric with the adhesive when going through the adhesive tank 4 with the adhesive coating scraper 5 and the coating adhesive coating roll 6, with the adhesive coating amount controlled by the adhesive coating scraper 5. Then laminate the nonwoven fabric and the base cloth with the press roll after superposing the nonwoven fabric and the base cloth according to the position relation of sandwiching the elastane yarn, and heat to evaporate water in the adhesive. Perform the press roll laminating and heating in a continuous laminating and drying way with the combination of the drying cylinder 8 and the four press rolls 7. That is, the nonwoven fabric, the elastane yarn and the base cloth are superposed and wound to go through the drying cylinder 8, and meanwhile the four press rolls 7 are positioned at exterior surface of the drying cylinder 8 in circumferential direction, such that the elastic base cloth is laminated on one side and heated on the other side when between the drying cylinder 8 and the press roll 7. In the process, pressure of the press roll is 2.5-3.5 kilograms, and the heating temperature is controlled at 80-120° C., so as to obtain composite elastic base cloth. Number of the press rolls 7 can be increased or reduced as needed, the pressure can be regulated via clearance between the drying cylinder 8 and the press roll 7, and the heating temperature is set via a heating source and a control system in the drying cylinder 8. The temperature and speed should be regulated such that water in the adhesive can be fully evaporated, and improvement of the production efficiency considered as far as possible.

Step two: Surface Treatment of Elastic Base Cloth

Although the elastic base cloth produced in Step one has many advantages, this approach will also impose an adverse influence on appearance and usage of the final product due to fiber on the exterior surface of the nonwoven fabric. The reason is that, on other hand, the nonwoven fabric itself is made of fiber, a fiber surface neither fine nor clean making the product appearance neither neat nor attractive; on the other hand, the exterior fiber surface of the nonwoven fabric coated with the adhesive may become more rough, even be torn, when the roll is dewound to use, affecting the usage property. In order to resolve the problem, the present invention, making use of the mechanism that natural latex, deproteinized latex or synthetic latex has a good film-forming characteristic, forms a protective film on the exterior surface of the nonwoven fabric through the surface treatment step of the elastic base cloth, thus obtaining a satisfactory effect. The specific contents are as below:

A. Raw Materials

Elastic Base Cloth.

Use natural latex, diluted with water according to latex:water=1:4, as a surface treatment agent for spare use. In view of anaphylaxis a few populations have for plant proteins, synthetic latex or deproteinized latex can also be chosen as a substitute for natural latex.

Use glacial acetic acid, diluted with water according to acid:water=1:10, as an acid curing agent for spare use. In view of low cost and high curing speed, hydrochloric acid can also be chosen as a substitute for glacial acetic acid.

B. Double-Sided Coating Process

Figure 2:
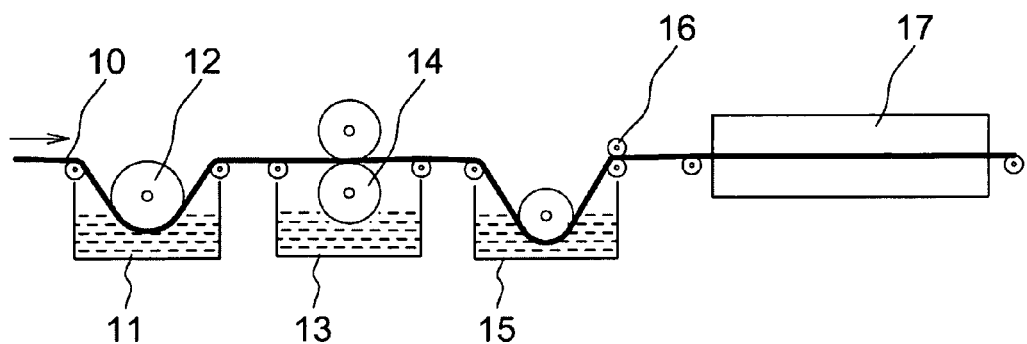
FIG. 2 is a schematic drawing of the surface treatment (double-sided coating) process flow of the elastic base cloth.
Figure 3:
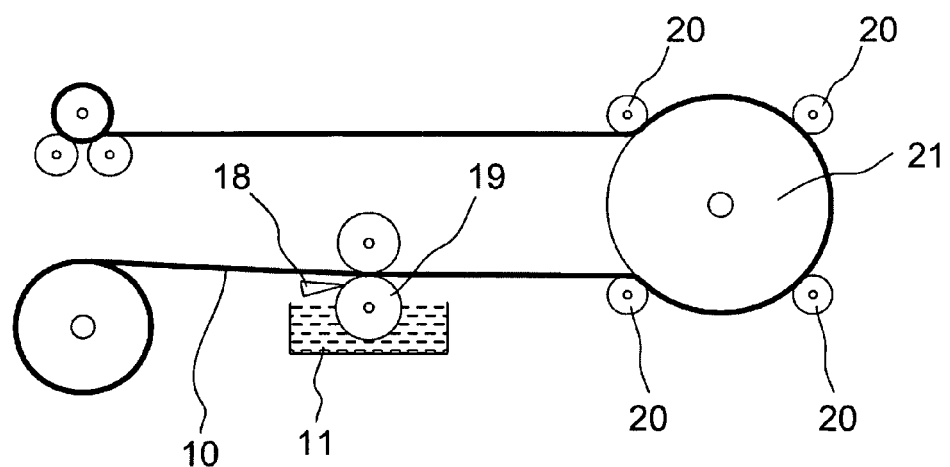
FIG. 3 is a schematic drawing of the surface treatment (single-sided coating) process flow of the elastic base cloth.

As shown in FIG. 2, dip coat the elastic base cloth 10 with the surface treatment agent by the dip roll 12 when the elastic base cloth 10 goes through the surface treatment agent tank 11 under the guidance of the guide roll. Then coat the exterior surface of the nonwoven fabric with the acid curing agent by the pick-up roll 14 when going through the acid curing agent tank 13. Then wash with water in the rinse tank 15. Finally dry by extruding with the press roll 16 and then sending to the oven 17. A temperature gradient with four segments is adopted in the oven from the inlet to the outlet, i.e., 144° C./127° C./129° C./120° C., with temperature accuracy for each segment controlled at ±15° C., most preferably ±10° C. In order to better regulate the acid vaporization, two cooling segments can be further added at the tail of the oven 17, with the temperatures at 50° C./60° C. The two temperature segments are provided just for improving odor of the elastic base cloth, with the accuracy controlled at 15° C.

Step three: Viscoelastic Treatment of Elastic Base Cloth

Step three is mainly for preventing difficulty in dewinding the elastic base cloth coated with the adhesive, making the product stripping as easy and uniform as possible and meanwhile the adhesive permeate to the other side of the elastic base cloth. The specific contents are as below:

A. Raw Materials

The elastic base cloth having received surface treatment.

Formulation of the anti-seizing treatment agent is as below:

| Composition | Content |
| --- | --- |
| Silicone rubber | 100 parts by weight |
| Methyltriethoxysilane | 35 parts by weight |
| Dibutyltin dilaurate | 8 parts by weight |
| 120# solvent gasoline | 800 parts by weight |

Following factors are generally considered in choosing the anti-seizing treatment agent:

a. Good insulation property, making the elastic bandage easy to be dewound; b. high binding force with a substrate, no transfer to the adhesive occurring during dewinding with a resulted lower viscosity; c. insulation property free from influence from amount of the coated anti-seizing treatment agent; d. good aging resistance, the insulation property not impaired due to prolonged action of high temperature and high humidity; and e. non-migration property.

B. Process

Figure 4:
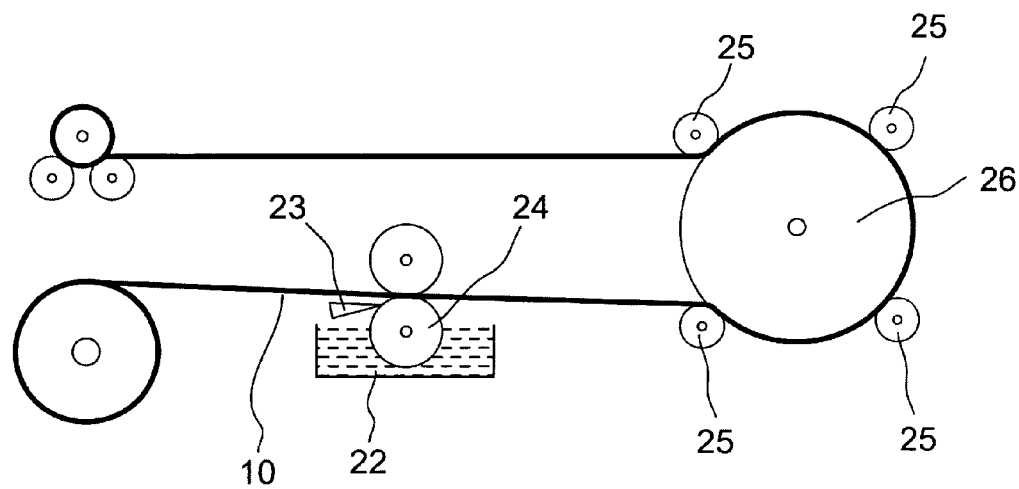
FIG. 4 is a schematic drawing of the anti-seizing treatment process flow of the elastic base cloth; and, FIG. 5 is a schematic drawing of the adhesive application process flow of the elastic base cloth.

As shown in FIG. 4, guide the elastic base cloth 10 having received surface treatment to the anti-seizing treatment agent tank 22 by the guide roll. Coat the exterior surface of the nonwoven fabric with the anti-seizing treatment agent by the pick-up scraper 23 and the pick-up roll 24. Then heat to evaporate solvent in the anti-seizing treatment agent through the continuous laminating and drying apparatus including the four press rolls 25 and the one drying cylinder 27, with the heating temperature controlled at 160-180° C.

Step four: Coating of Elastic Base Cloth with Adhesive

A. Raw Materials

The elastic base cloth having received the anti-seizing treatment.

Use a hot melt adhesive as the adhesive. Advantages of the hot melt adhesive: a. 100% solid, no solvent, energy saving, pollution free, and nonpoisonous; b. fast curing, high production efficiency, and suitable for an industrialized mass production; c. stable property, and convenient for packaging, storing, transporting and using; d. allow repeated heating and bonding, scrap free, and easy removal of the adhesive; and e. resistant against water, acid, oil, etc. The hot melt adhesive can be classified into the following types according to base stock:

a. Ethylene Vinyl Acetate Copolymer (EVA) Type
b. Polyamide (PA) type
c. Polyester (PET) type
d. Polyurethane (PU) type
e. Block polymer (SDS) type
f. Polyolefin (PO) type This embodiment chooses a hot melt adhesive of the block polymer (SDS) type.

B. Process

Figure 5:
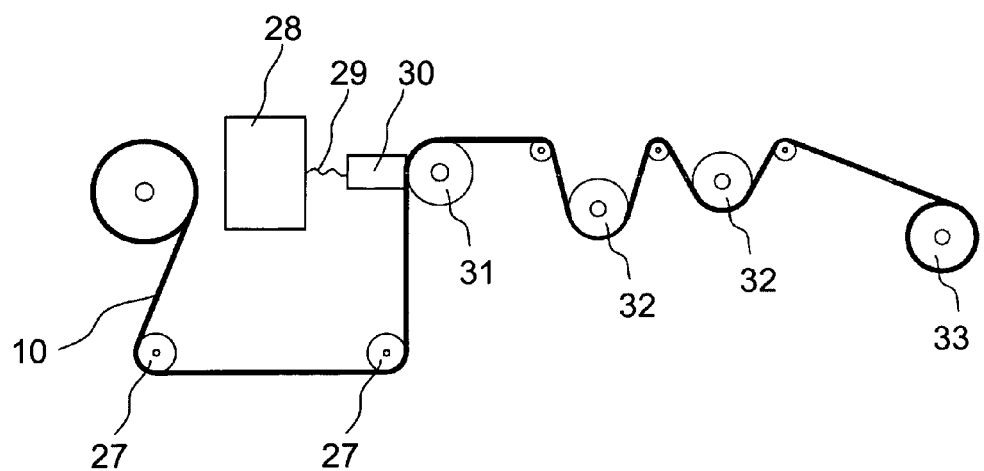

As shown in FIG. 5, guide the elastic base cloth 10, having received the anti-seizing treatment in the last step, with the guide roll 27 to the adhesive coating apparatus including the adhesive box 28, the pipe 29, the adhesive nozzle 30 and the adhesive coating roll 31. Heat to melt the hot melt adhesive in the adhesive box 28 and, after its flowing through the pipe 29 to the adhesive nozzle 30, spray it through the adhesive nozzle 30 onto the exterior surface of the base cloth of the elastic base cloth 10 in a liquid form. Then cool off with the rear two cooling rolls 32, and slit according to a certain width and length. Obtain the final product through winding up with the wind-up roll 33.

The individual process step in the embodiment, manufacture of elastic base cloth→surface treatment of elastic base cloth→anti-seizing treatment of elastic base cloth→coating of elastic base cloth with adhesive, can either be linked together into a consecutive production line, or form independently individual production line.

The above embodiment is used only for explaining the technical concept and characteristics of the present invention. It is provided to make those skilled in the art understand the present invention and implement it, and cannot thereby limit the extent of protection of the present invention. All equivalent changes or modifications according to the spirit of the present invention should fall within the extent of protection of the present invention.

| Reference Numbers | |
|---|---|
| 1 | nonwoven send roll |
| 2 | elastane yarn send roll |
| 3 | base cloth send roll |
| 4 | adhesive tank |
| 5 | adhesive coating scraper |
| 6 | adhesive coating roll |
| 7 | press roll |
| 8 | drying cylinder |

| Reference Numbers | |
|---|---|
| 9 | wind-up roll |
| 10 | elastic base cloth |
| 11 | surface treatment agent tank |
| 12 | dip roll |
| 13 | acid curing agent tank |
| 14 | pick-up roll |
| 15 | rinse tank |
| 16 | press roll |
| 17 | oven |
| 18 | adhesive coating scraper |
| 19 | adhesive coating roll |
| 20 | press roll |
| 21 | drying cylinder |
| 22 | anti-seizing treatment agent tank |
| 23 | pick-up scraper |
| 24 | pick-up roll |
| 25 | press roll |
| 26 | drying cylinder |
| 27 | guide roll |
| 28 | adhesive box |
| 29 | pipe |
| 30 | adhesive nozzle |
| 31 | adhesive coating roll |
| 32 | cooling roll |
| 33 | wind-up roll |

What is claimed is:

1. A method of manufacturing a laminated viscoelastic bandage, wherein the manufacturing method includes the following sequential steps:

(1) manufacturing of an elastic base cloth lamination by the steps of:

providing a non-woven fabric, elastic yarn, a base cloth and an adhesive, the adhesive comprising natural or synthetic latex diluted with water in a ratio of latex to water of 1:1-2;

feeding a nonwoven fabric, a elastic yarn and a base cloth through different send rolls; coating an interior surface of either one of the nonwoven fabric or the base cloth with the adhesive; superposing the non-woven fabric and the base cloth with the elastic thereby sandwiching the elastic yarn between the non-woven fabric and the base cloth to form a lamination; laminating the non-woven fabric and the base cloth with a press roll; and simultaneously heating and pressing the lamination to evaporate water in the adhesive, so as to obtain composite elastic base cloth; wherein the pressure of the press roll lies between 2-4 kilograms and the heating temperature lies between 80-180° C.;

(2) surface treating the manufactured elastic base cloth by the steps of providing a surface treatment agent comprising natural latex or deproteinized latex or synthetic latex diluted with water according to a ratio of latex to water of 1:2-6, an acid curing agent comprising glacial acetic acid or hydrochloric acid diluted with water according to a ratio of acid:water of 1:8-12;

choosing one of the following two surface treatment processes for the elastic base cloth lamination;

a. double-sided coating guiding the elastic base cloth lamination;

dip coating the elastic base cloth composite with the surface treatment agent in a tank; coating at least the exterior surface of the nonwoven fabric with the acid curing agent to cure; washing the elastic base cloth composite with water in a rinse tank; and extruding the elastic base cloth composite with the press roll; drying in an oven wherein—the oven temperature lies between 80-180° C.;

b. single-sided coating coating the exterior surface of the nonwoven fabric with the surface treatment agent; and, heating the elastic base cloth to evaporate water in the surface treatment agent, with the heating temperature controlled at between 80-180° C.;

wherein the elastic base cloth is guided by a guide roll;

(3) third step: anti-seizing treatment of the elastic base cloth got from the second step providing an anti-seizing treatment agent, formulation of the anti-seizing treatment agent is as below:

| Composition | Content |
|---|---|
| silicone rubber | 100 parts by weight ± 10%; |
| methyltriethoxysilane | 35 parts by weight ± 10%; |
| dibutyltin dilaurate | 8 parts by weight ± 10%; |
| 120# solvent gasoline | 800 parts by weight ± 10%; | coating an exterior surface of the nonwoven fabric with the anti-seizing treatment agent; and, heating to evaporate solvent in the anti-seizing treatment agent with the heating temperature lying between 130-200 degrees C.;

wherein the elastic base cloth is guided by a guide roll;

(4) coating of elastic base cloth with adhesive providing a hot melt adhesive, a water-based adhesive or a solvent adhesive as an adhesive;

coating one side of the elastic base cloth from the anti-seizing treatment, with the adhesive;

supplying after-treatment to the elastic base cloth from the anti-seizing treatment;

and winding elastic base cloth from the anti-seizing treatment;

wherein the elastic base cloth from the anti-seizing treatment is guided with a guide roll.

2. The method of manufacturing a laminated viscoelastic bandage as recited in claim 1, wherein the manufacturing process is a continuous process with the combination of a drying cylinder and the press roll; wherein the nonwoven fabric, the elastic yarn and the base cloth are superposed and wound to go through the drying cylinder, and press rolls are positioned at the exterior surface of the drying cylinder in circumferential direction, such that the elastic base cloth is laminated on one side and heated on the other side when between the drying cylinder and the press roll.

3. The method of manufacturing a laminated viscoelastic bandage as recited in claim 1, wherein in the surface treatment of the elastic base cloth, a temperature gradient with at least two segments is adopted in the oven from the inlet to the outlet;

wherein the temperature range is controlled at 100-160° C.

* * * * *